(12) United States Patent
Yang et al.

(10) Patent No.: US 7,113,274 B2
(45) Date of Patent: Sep. 26, 2006

(54) METHOD AND APPARATUS FOR INSPECTING A SUBSTRATE

(75) Inventors: Yu-Sin Yang, Seoul (KR); Sang-Mun Chon, Kyunggi-do (KR); Sun-Yong Choi, Kyunggi-do (KR); Chung-Sam Jun, Kyunggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 346 days.

(21) Appl. No.: 10/777,922

(22) Filed: Feb. 11, 2004

(65) Prior Publication Data

US 2004/0169851 A1     Sep. 2, 2004

(30) Foreign Application Priority Data

Feb. 28, 2003   (KR)   ...................... 10-2003-0012824

(51) Int. Cl.
*G01N 21/00* (2006.01)

(52) U.S. Cl. .................................................. 356/237.1

(58) Field of Classification Search ............. 356/237.3, 356/237.2, 237.4, 237.5, 239.1, 239.3, 237.1; 250/559.4, 559.41, 559.42, 559.45
See application file for complete search history.

(56) References Cited

U.S. PATENT DOCUMENTS

| | | | |
|---|---|---|---|
| 5,179,422 A * | 1/1993 | Peterson | 356/237.1 |
| 5,563,702 A * | 10/1996 | Emery et al. | 356/73 |
| 5,663,569 A * | 9/1997 | Hayano | 250/559.45 |
| 5,909,276 A * | 6/1999 | Kinney et al. | 356/237.2 |
| 6,215,551 B1 | 4/2001 | Nikoonahad et al. | |
| 6,654,112 B1 * | 11/2003 | Noguchi et al. | 356/237.3 |
| 2003/0086080 A1 * | 5/2003 | Guan et al. | 356/237.1 |

* cited by examiner

*Primary Examiner*—Hoa Pham
*Assistant Examiner*—Tri Ton
(74) *Attorney, Agent, or Firm*—Marger Johnson & McCollm, P.C.

(57) ABSTRACT

In a method and an apparatus for inspecting defects on a substrate using a light beam, a light source irradiates light beams having different wavelengths onto the substrate. A detector detects first lights scattered from a surface of the substrate and second lights scattered from impurities on the substrate by irradiation of the light beams. An operation unit compares first intensities of the first lights with second intensities of the second lights in order to produce differential values therebetween, and selects a wavelength corresponding to a maximum value of the differential values. An inspection process for inspecting the defects on the substrate is performed using a light beam having the selected wavelength.

20 Claims, 6 Drawing Sheets

METHOD AND APPARATUS FOR INSPECTING A SUBSTRATE

RELATED APPLICATION

The present application claims priority from Korean Patent Application No. 2003-12824, filed Feb. 28, 2003, the disclosure of which is incorporated herein by reference in its entirety.

FIELD OF THE INVENTION

The present invention relates to a method and an apparatus for inspecting a substrate, and more particularly, to a method and an apparatus for inspecting defects on a semiconductor substrate using a light scattered from a surface of a semiconductor substrate by irradiation of a light beam.

DESCRIPTION OF THE RELATED ART

Generally, semiconductor devices are manufactured through a three-step process. First, a fabrication process is performed for forming electronic circuits on a silicon wafer used as a semiconductor substrate. Second, an electrical die sorting (EDS) process is performed for inspecting electrical characteristics of the semiconductor devices on the semiconductor substrate. Third, a packaging process is performed for packaging the semiconductor devices in epoxy resins and individuating the semiconductor devices.

The fabrication process for producing a semiconductor device may include any of the following: a deposition process for depositing a layer of a selected material onto the semiconductor substrate, a chemical mechanical polishing (CMP) process for planarizing a surface of the layer, a photolithography process for forming a photoresist pattern on the layer, an etching process for forming a predetermined pattern using a patterned photoresist material in the semiconductor substrate, an ion implantation process for implanting predetermined ions into predetermined portions of the semiconductor substrate, a cleaning process for removing impurities from the semiconductor substrate, an inspection process for inspecting defects on the semiconductor substrate on which the layer or the pattern is formed, or other similar processes.

Defects, such as impurities remaining on the surface of the semiconductor substrate, deteriorate the performance of the semiconductor devices as well as lower yields in the manufacturing of the semiconductor devices. Recently, as the degree of integration of the semiconductor devices has increased, the inspection process for these defects has become increasingly important in the manufacturing of the semiconductor devices.

For example, U.S. Pat. No. 6,215,551 (Nikoonahad, et al.) discloses a scanning system for inspecting anomalies on surfaces. The scanning system directs a focused beam of light at a grazing angle toward the surface to be inspected, and collects the light scattered along the scan path for detecting the anomalies.

While the light beam is irradiated onto the semiconductor substrate, an intensity of a light scattered from the semiconductor substrate is varied in accordance with materials of layers or patterns on the semiconductor and a wavelength of a light beam.

Figure 1:
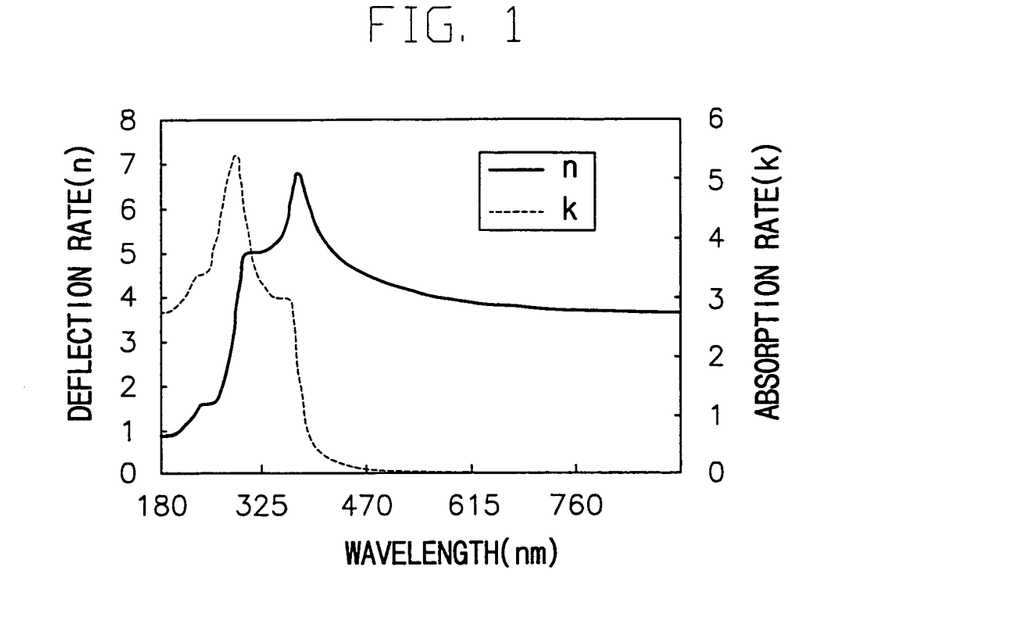
FIG. 1 is a line graph showing a light deflection rate and a light absorption rate on a silicon wafer.
Figure 2:
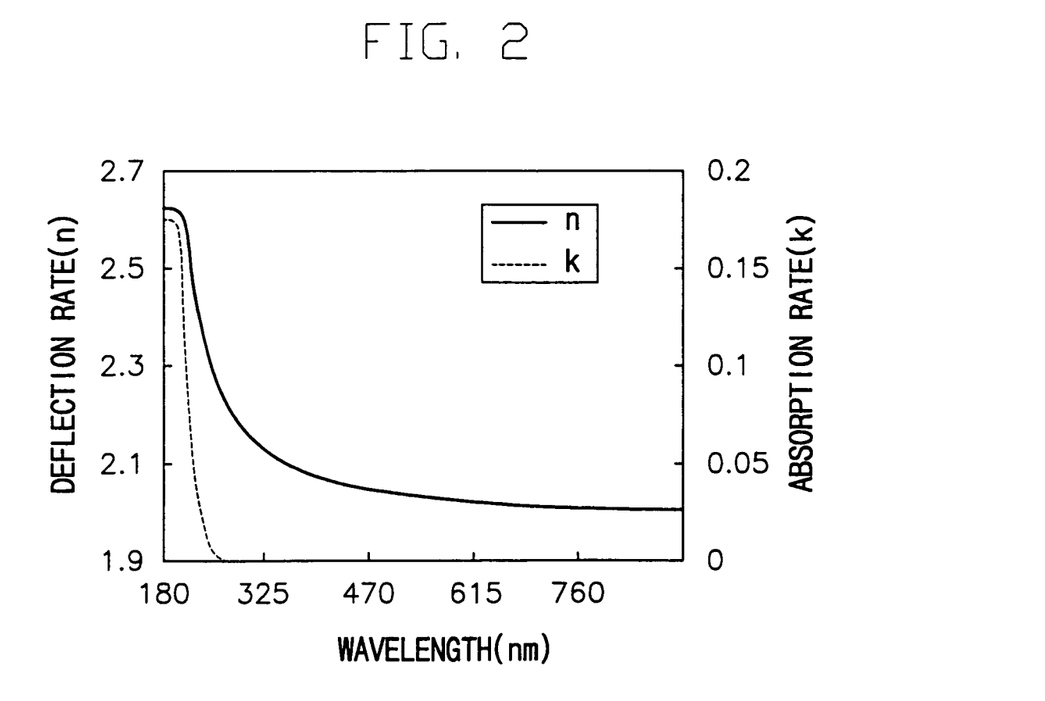
FIG. 2 is a line graph showing a light deflection rate and a light absorption rate on a nitride layer.
Figure 3:
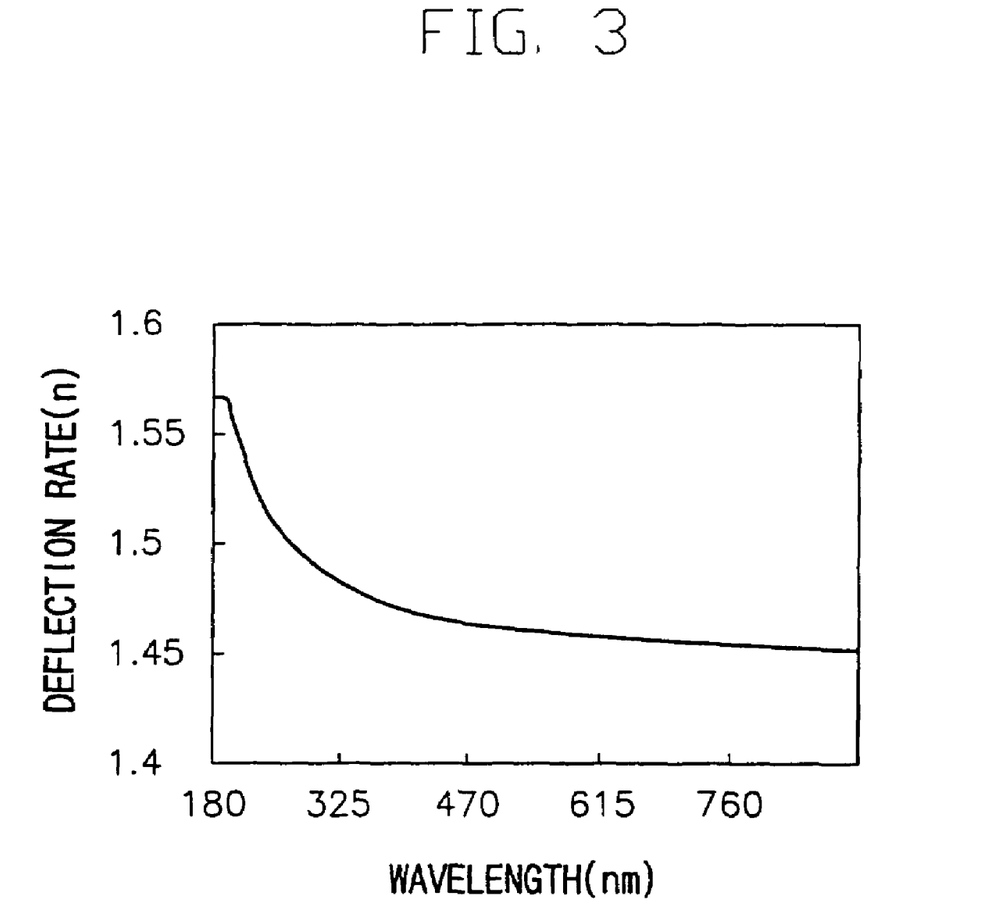
FIG. 3 is a line graph showing a light deflection rate on an oxide layer.

FIG. 1 is a line graph showing a light deflection rate and a light absorption rate on a silicon wafer. FIG. 2 is a line graph showing a light deflection rate and a light absorption rate on a nitride layer. FIG. 3 is a line graph showing a light deflection rate on an oxide layer.

Referring to FIGS. 1 to 3, a light deflection rate and a light absorption rate are varied in accordance with a wavelength of a light beam and materials of objects. Thus, a light scattering rate of a light beam having a specific wavelength is varied in accordance with the materials of the objects.

A conventional apparatus employs a laser beam having a predetermined specific wavelength, and thus the reliability of the inspection process is deteriorated. That is, an intensity of a light scattered from the semiconductor substrate by irradiation of the laser beam having the specific wavelength is varied in accordance with the layers or the patterns formed on the semiconductor substrate. For example, an intensity of a light scattered from the oxide layer on the semiconductor substrate, and an intensity of a light scattered from the nitride layer on the semiconductor substrate, are different from each other. Accordingly, detection rates of the impurities remaining on the oxide layer and the nitride layer become different from each other. The reliability of the inspection process is also deteriorated because the intensity of the light scattered from the semiconductor substrate is varied in accordance with the specific materials which comprise the impurities.

SUMMARY OF THE INVENTION

According to embodiments of the present invention, a method and an apparatus may be provided to select a wavelength of a light beam in accordance with materials of layers or patterns formed on a semiconductor substrate and materials of impurities remaining on the semiconductor substrate, and to inspect defects on the semiconductor substrate using a light beam having the selected wavelength.

According to method embodiment of the present invention, a method for inspecting a substrate comprises irradiating first light beams onto the substrate, the first light beams having different wavelengths, detecting first intensities of first lights scattered from a surface of the substrate and detecting second intensities of second lights scattered from impurities on the substrate, comparing the first intensities of the first lights with the second intensities of the second lights in order to produce differential values between the first and second intensities, irradiating a second light beam onto the substrate, the second light beam having a wavelength corresponding to a maximum value of the differential values, and inspecting the substrate for defects by examining a third light scattered from the surface of the substrate and a fourth light scattered from the impurities on the substrate.

The substrate may include a semiconductor substrate such as a semiconductor wafer, and laser beams may be employed as the first light beams and second light beam. The first light beams are preferably sequentially irradiated by a predetermined wavelength onto the substrate. Lights scattered from the substrate can be detected by a detector. The first intensities and second intensities are varied in accordance with the wavelengths of the first light beams.

The selected wavelength corresponds to the maximum value of the differential values between the first and second intensities. Thus, when an inspection process for inspecting the defects on the substrate is performed using the second light beam having the selected wavelength, the efficiency of the inspection process may be improved. That is, the impurities on the substrate may be easily detected using the third light scattered from the surface of the substrate and the fourth light scattered from the impurities on the substrate by irradiation of the second light beam.

According to another embodiment of the present inventing, an apparatus for inspecting a substrate comprises a light source for irradiating a plurality of light beams onto the substrate, the plurality of light beams having different wavelengths, a detector for detecting lights scattered from the substrate, an operation unit for comparing first intensities of first lights scattered from a surface of the substrate with second intensities of second lights scattered from impurities on the substrate, for producing differential light intensity values between the first intensities and the second intensities, and for selecting a wavelength corresponding to a maximum value of the differential values, a controller for controlling operation of the light source such that the plurality of light beams is sequentially irradiated onto the substrate, and a selected light beam having the selected wavelength is irradiated onto the substrate, and an image processing unit for acquiring an image representing the substrate using a light scattered from substrate by irradiation of the selected light beam, and for inspecting defects of the substrate from the image.

DESCRIPTION OF THE PREFERRED EMBODIMENTS

The present invention now will be described more fully hereinafter with reference to the accompanying drawings in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 4:
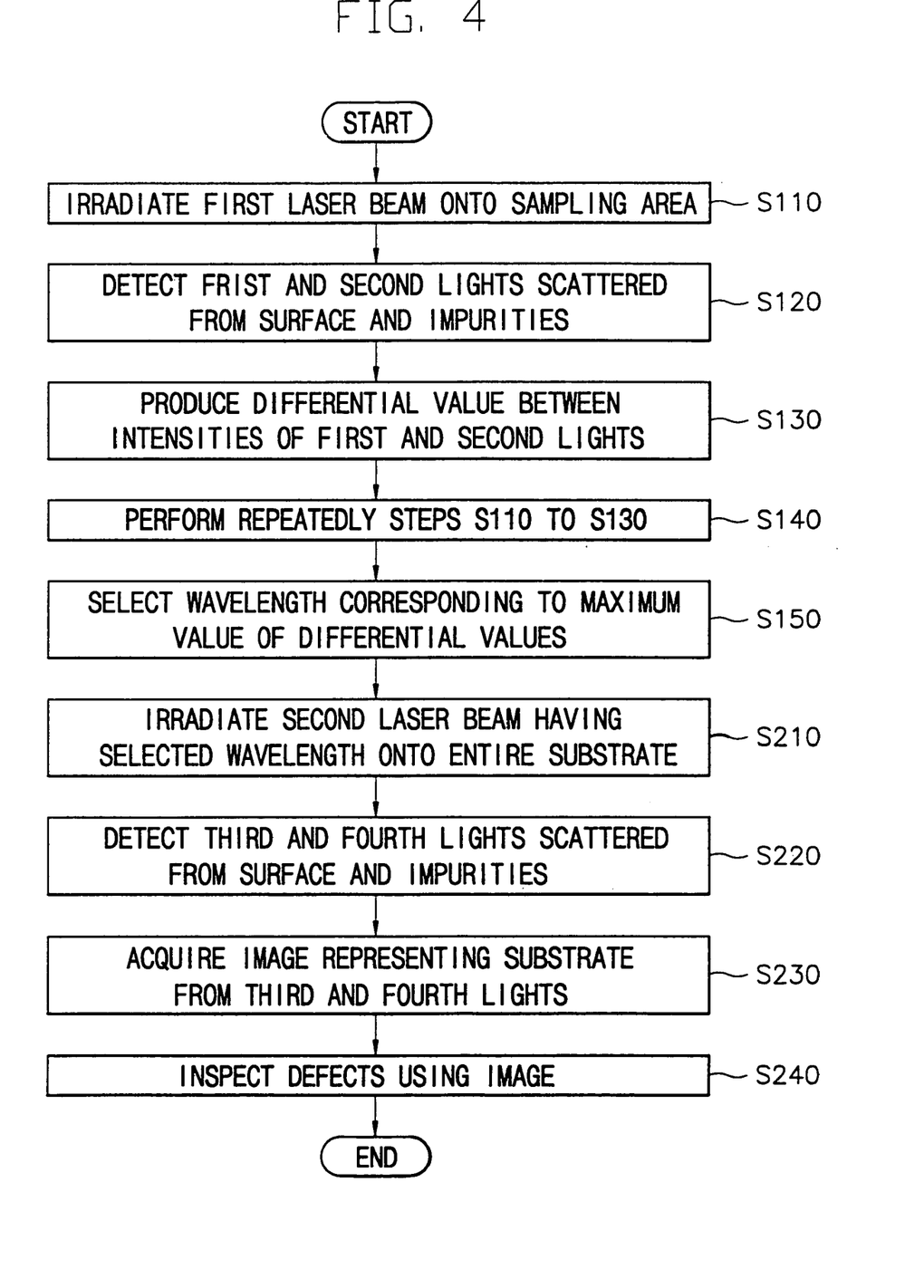
FIG. 4 is a flow chart illustrating a method for inspecting a semiconductor substrate according to an embodiment of the present invention.

Referring to FIG. 4, the substrate inspection method preferably includes a first process for selecting an inspection wavelength among first wavelengths of first light beams, and a second process for inspecting defects, such as impurities on the substrate surface, using a second light beam having a selected wavelength. Laser beams having different wavelengths are preferably employed as the first light beams and for the second light beam. The substrate preferably comprises a semiconductor substrate, such as a silicon wafer, on which layers and/or patterns are formed.

The first process includes steps S110 to S150.

In step S110, a light source irradiates a first laser beam onto a predetermined sampling area of the semiconductor substrate. The first laser beam scans the sampling area in an x-direction. The semiconductor substrate is moved in a y-direction. The x-direction and the y-direction cross each other perpendicularly. A tunable optical parametric oscillator laser system may be used as the light source.

In next step S120, a detector detects a first light scattered from a surface of the sampling area and a second light scattered from impurities remaining on the sampling area in response to the irradiation of the first laser beam.

Subsequently, in step S130, an operation unit compares a first intensity of the first light with a second intensity of the second light in order to produce a differential value between the first and second light intensities.

The steps S110 to S130 are repeatedly performed when a first wavelength of the first light beam is sequentially varied by a predetermined wavelength in step S140. The first wavelength may be varied between about 250 nm to about 700 nm. Preferably, the first wavelength may be varied between about 250 nm to about 400 nm. More preferably, the first wavelength can be varied between the above wavelengths by a predetermined wavelength of about 10 nm.

In step S150, the operation unit then selects a second wavelength corresponding to a maximum value of the differential values produced during the steps S110 to S140 above.

The second process includes steps S210 to S240.

In step S210, the light source irradiates a second laser beam having the second wavelength onto the entire semiconductor substrate. The second laser scans the entire semiconductor substrate in the x-direction, and the semiconductor substrate moves in the y-direction.

In sequent step S220, the detector detects a third light scattered from a surface of the semiconductor substrate and a fourth light scattered from impurities on the semiconductor substrate by irradiation of the second laser beam.

An image processing unit acquires an image representing the semiconductor substrate in step S230. A third intensity of the third light and a fourth intensity of the fourth light are converted into electric signals by the detector, respectively. The image processing unit acquires the image based on the electric signals, and a display unit displays the image.

The image processing unit inspects the defects on the semiconductor substrate by analyzing the image in step S240. A differential value between the third and fourth intensities corresponds to the maximum value of the differential values between the first and second intensifies. Thus, the impurities on the semiconductor substrate may be readily detected, and the efficiency of the inspection process may be improved.

Referring to FIGS. 5 to 7B, the substrate inspection apparatus 100 preferably includes a laser source 110 for generating a laser beam 20, a detector 120 for detecting a light 30 scattered from a semiconductor substrate 10, an operation unit 130 for analyzing intensities of the scattered light 30, a controller 140 for controlling the operation of the laser source 110, and an image processing unit 150 for receiving an image representing the semiconductor substrate 10 using the intensity of the scattered light 30.

Figure 5:
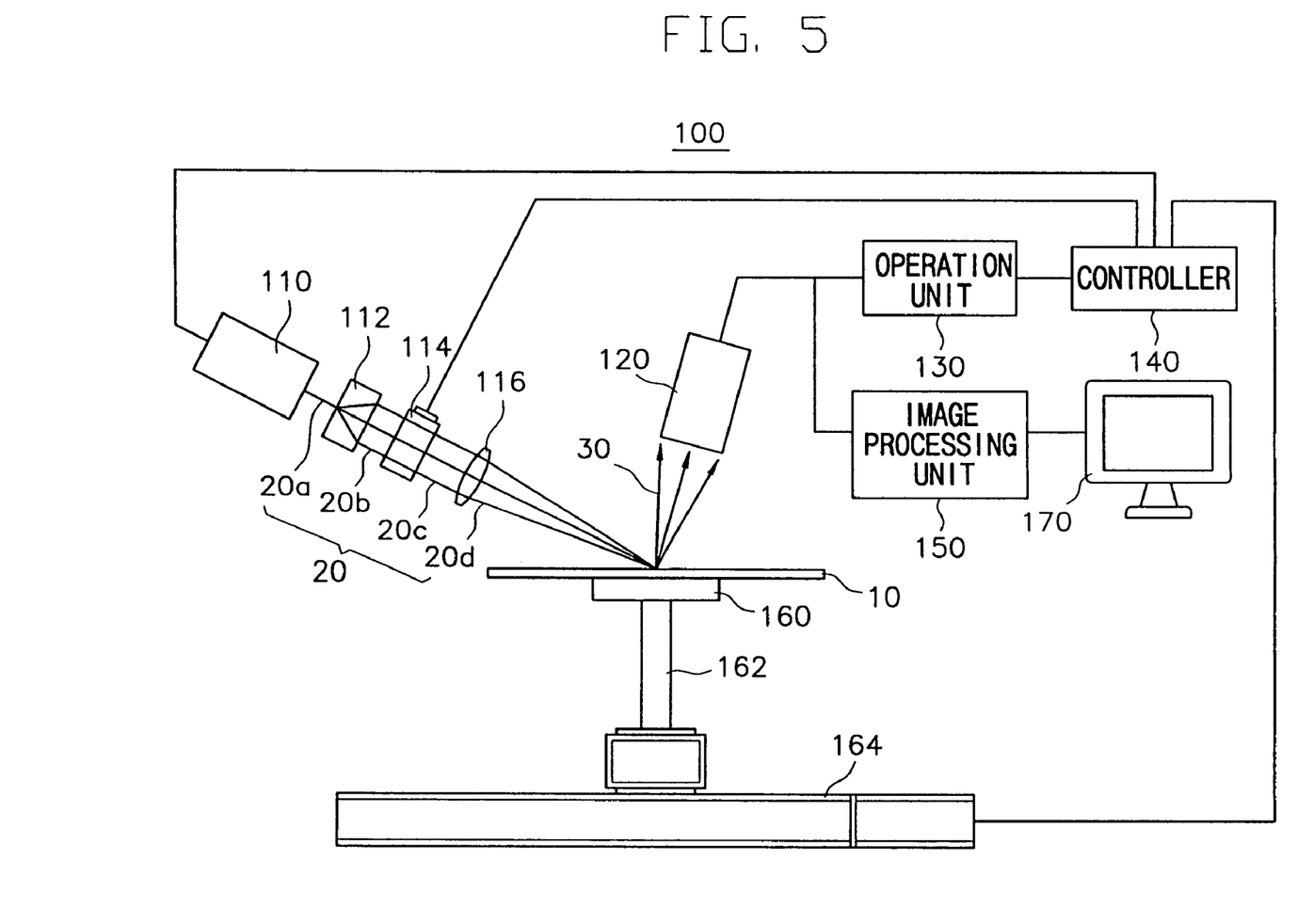
FIG. 5 is a schematic view of an apparatus for performing the method as shown in FIG. 4.

The laser source 110 irradiates laser beams having different wavelengths onto the semiconductor substrate 10. For example, the laser source 110 sequentially varies a wavelength of the laser beam 20 by a predetermined wavelength while the laser beam 20 is irradiated onto semiconductor substrate 10. A turnable optical parametric oscillator laser system may be preferably used as the laser source 110. The tunable optical parametric oscillator laser system is able to vary the wavelength of the laser beam 20 at discrete intervals either by a predetermined wavelength or linearly. The wavelength of the laser beam 20 may be varied between about 250 nm to about 700 nm, preferably between about 250 nm to about 400 nm. More preferably, the wavelength of the laser beam 20 may be varied by a predetermined wavelength of about 10 nm.

A moving stage 160 supports the semiconductor substrate 10 thereon. The moving stage 160 moves the semiconductor substrate 10 in a horizontal direction so that the laser beam 20 scans a surface 10a of the semiconductor substrate 10. A driving shaft 162 connects the moving stage 160 with a driving unit 164 for moving the moving stage 160.

The driving unit 164 preferably includes a Cartesian robot. The driving unit 164 moves the moving stage 160 in the x-direction and the y-direction so that the laser beam 20 scans a predetermined sampling area 12 of the semiconductor substrate 10 or an entire surface of the semiconductor substrate 10.

A beam expander 112 expands a cross-sectional area of the laser beam 20a generated by the laser source 110. A beam deflector 114 deflects the laser beam 20b expanded by the beam expander 112 so that the laser beam 20 scans the surface 10a of the semiconductor substrate 10. A focusing lens 116 focuses the deflected laser beam 20c onto the surface 10a of the semiconductor substrate 10 such that a spot size of the laser beam 20d irradiated onto semiconductor substrate 10 may be evenly maintained.

The detector 120 detects the lights 30 scattered from the semiconductor substrate 10 by irradiation of the laser beams, converts the detected lights 30 into electric signals, and sends the electric signals to the operation unit 130 and the image processing unit 150.

Figure 7A:
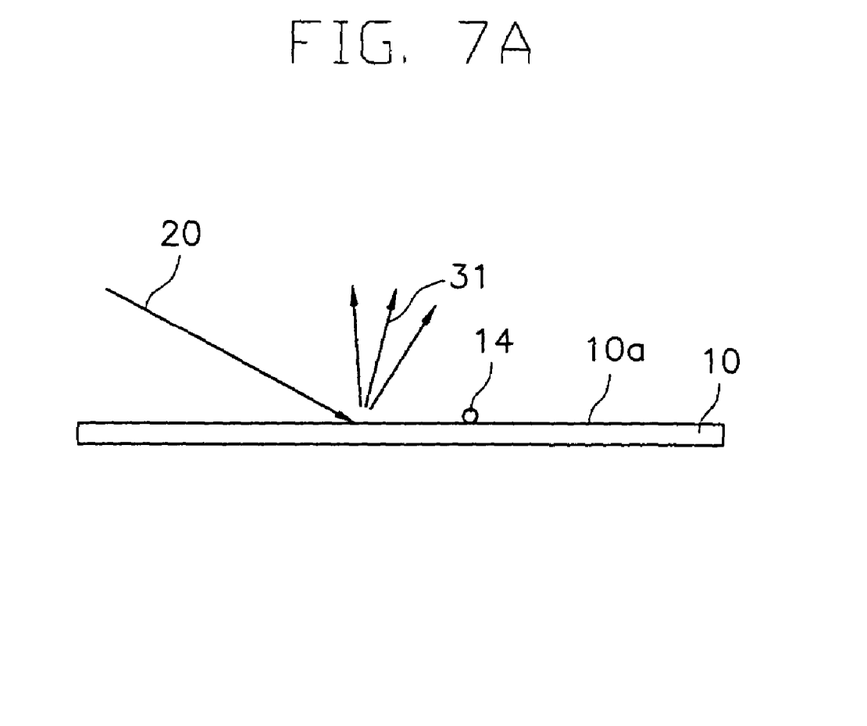
FIGS. 7A and 7B are front views illustrating a first light and a second light scattered from the semiconductor substrate.
Figure 7B:
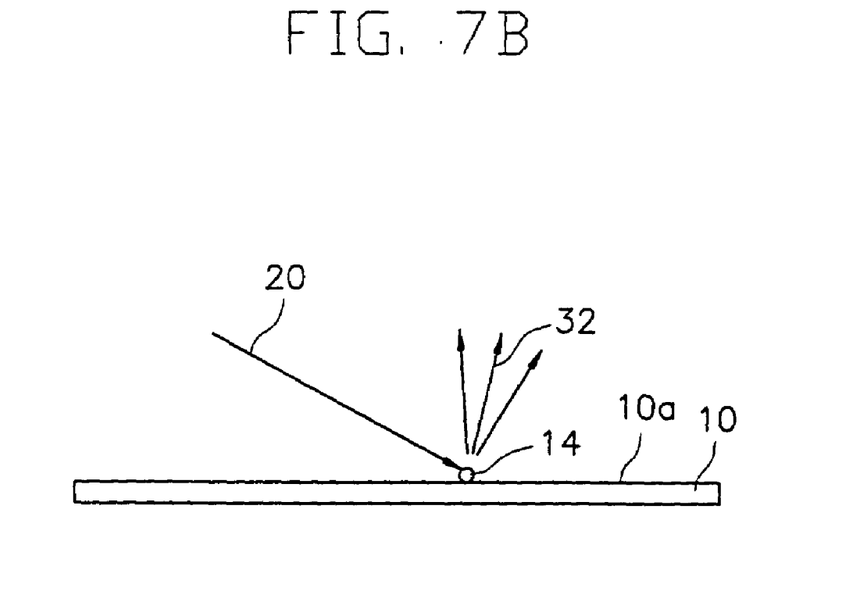

The operation unit 130 compares the first intensities of the first lights 31 scattered from the surface 10a of the semiconductor substrate 10 with second intensities of second lights 32 scattered from the impurities 14 on the semiconductor substrate 10 based on the respective electric signals. Also, the operation unit 130 produces differential values between the first and second intensities, and then selects an inspection wavelength corresponding to a maximum value of these differential values.

Figure 6:
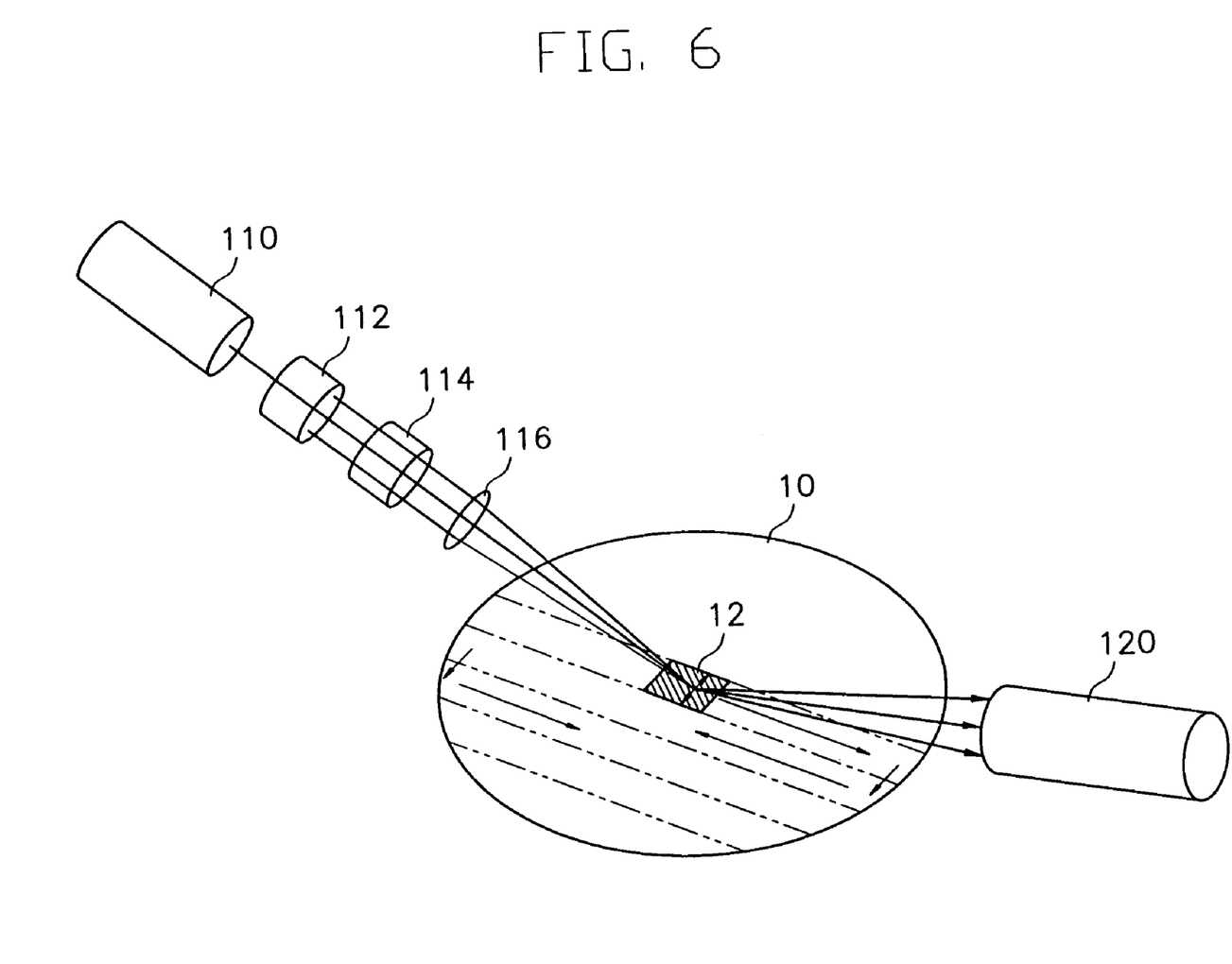
FIG. 6 is a perspective view of the apparatus as shown in FIG. 5.

The controller 140 is connected to the operation unit 130. The controller 140 controls operation of the laser source 110 so as to irradiate the laser beams onto the sampling area 12 sequentially by the predetermined wavelength, and to irradiate an inspection laser beam having the selected inspection wavelength onto the entire surface of the semiconductor substrate 10. Also, the controller 140 controls operations of the beam deflector 114 and the driving unit 164 such that the laser beams and the inspection laser beam scan the surface of the sampling area 12 and the entire surface of the semiconductor substrate 10, respectively, as shown in FIG. 6.

The image processing unit 150 acquires the image representing the semiconductor substrate 10, and the display unit 170 displays the image. Also, the image processing unit 150 detects positions and sizes of the impurities remaining on the semiconductor substrate 10 from the image.

A method for inspecting defects, such as the impurities, on the semiconductor substrate 10 using the substrate inspection apparatus 100 will be described hereinafter with reference to FIGS. 5 to 7B.

The semiconductor substrate 10 is supported on the moving stage 160. The beam expander 112 expands the cross-section area of the first laser beam generated from the laser source 110. The expanded first laser beam is irradiated onto the sampling area 12 through the beam deflector 114 and the focusing lens 116. The beam deflector 114 deflects the first laser beam so that the first laser beam scans the sampling area 12 in the x-direction. The driving unit 164 moves the moving stage 160 so that the first laser beam scans the sampling area 12 in the y-direction.

The detector 120 detects the first light scattered from the surface of the sampling area 12 and the second light scattered from the impurities on the sampling area 12. Also, the detector 120 converts the first intensity of the first light and the second intensity of the second light into first electric signals, and sends the first electric signals to the operation unit 130.

The operation unit 130 compares the first electric signals to each other in order to produce the differential value between the first electric signals.

The laser source 110 increases the first wavelength of the first laser beam by the predetermined wavelength. The first laser beam having an increased first wavelength is irradiated onto the sampling area 12 through the beam expander 112, the beam deflector 114 and the focusing lens 116. The differential value corresponding to the increased first wavelength may be produced by the detector 120 and analyzed by the operation unit 130 in such a manner as described herein.

The differential values between the first lights and the second lights are produced sequentially during the variation of the first wavelength. The detector 120 detects the first intensity variation of the first light and the second intensity variation of the second light during the variation of the first wavelength.

The operation unit 130 produces a plurality of differential values from the first and second intensity variations, and selects the maximum value from the plurality of differential values thus produced.

The controller 140 controls the operation of the laser source 110 so as to generate the second laser beam having the second wavelength corresponding to the maximum value. Also, the controller 140 controls the operation of the beam deflector 114 so that the second laser beam scans the surface of the semiconductor substrate 10 in the x-direction. Furthermore, the controller 140 controls operation of the driving unit 164 so that the second laser beam scans the entire surface of the semiconductor substrate 10 in the x and y directions as shown in FIG. 6.

The detector 120 detects the third light scattered from the surface of the semiconductor substrate 10 and the fourth light scattered from the impurities on the semiconductor substrate 10. Also, the detector 120 converts the third intensity of the third light and the fourth intensity of the fourth light into second electric signals, and sends the second electric signals to the image processing unit 150.

The image processing unit 150 acquires the image representing the semiconductor substrate 10 using the second electric signals, and the display unit 170 displays the image. The image processing unit 150 detects the impurities remaining on the semiconductor substrate 10 by analyzing the image.

A differential value between the third intensity and the fourth intensity is typically larger than the differential values between the first intensities and the second intensities. As a result, the impurities on the semiconductor substrate 10 may be readily detected.

According to exemplary embodiment of the present invention, the inspection laser beam having the selected inspection wavelength may improve the efficiency and reliability in the process for inspecting the defects on the semiconductor substrate.

In the drawings and specification, there have been disclosed typical preferred embodiments of the invention, and although specific terms are employed, they are used in a generic and descriptive sense only and not for purposes of limitation, the scope of the invention being set forth in the following claims.

What is claimed is:

1. A method for inspecting a substrate for defects, the method comprising:
   irradiating a plurality of light beams onto the substrate, the a plurality of light beams having different wavelengths;
   detecting first intensities of first lights scattered from a surface of the substrate, and detecting second intensities of second lights scattered from impurities on the substrate;
   comparing the first intensities of the first lights with the second intensities of the second lights in order to determine differential values between the respective first and second intensities;
   irradiating a selected light beam onto the substrate, the selected light beam having a wavelength corresponding to a maximum value of the differential values between the respective first and second intensities; and
   inspecting the substrate for defects by examining a third light scattered from the surface of the substrate and a fourth light scattered from the impurities on the substrate.

2. The method of claim 1, wherein the plurality of light beams are irradiated onto a sampling area on the substrate.

3. The method of claim 1, wherein the wavelengths of the plurality of light beams are in a range of about 250 nm to about 700 nm.

4. The method of claim 1, wherein the inspecting includes:
   receiving an image representing the substrate from the third and fourth scattered lights; and
   detecting the defects of the substrate based on the image received.

5. The method of claim 4, further comprising displaying the image.

6. A method for inspecting a substrate for defects comprising: irradiating a first light beam onto a sampling area on the substrate;
   varying a first wavelength of the first light beam;
   detecting a first intensity variation of a first light scattered from a surface of the sampling area and a second intensity variation of a second light scattered from impurities on the sampling area during variation of the first wavelength;
   comparing the first intensity variation with the second intensity variation in order to produce differential light intensity values between first intensities and second intensities corresponding to the first and second intensity variations, respectively;
   irradiating a second light beam onto the substrate, the second light beam having a second wavelenglh corresponding to a maximum value of the differential light intensity values; and
   inspecting defects of the substrate using a third light scattered from a surface of the substrate and a fourth light scattered from impurities on the substrate.

7. The method of claim 6, wherein the first wavelength is varied by a discrete amount.

8. The method of claim 6, wherein the first wavelength is sequentially varied by a predetermined amount.

9. The method of claim 6, wherein the first wavelength is varied between about 250 nm to about 400 nm.

10. The method of claim 6, wherein the first and second light beams scan the sampling area on the substrate and the entire substrate, respectively.

11. The method of claim 6, wherein the inspecting includes:
    receiving an image representing the substrate from the third and fourth lights; and
    detecting the defects of the substrate based on the image received.

12. The method of claim 11, further comprising displaying the image.

13. A method for inspecting a substrate comprising:
    irradiating a first light beam onto a sampling area on the substrate;
    detecting a first light scattered from a surface of the sampling area and a second light scattered from impurities on the sampling area;
    producing a differential value of light intensity between a first intensity of the first light and a second intensity of the second light;
    repeatedly irradiating the first light beam in which a first wavelength of the first light beam is sequentially varied by a predetermined amount;
    selecting a second wavelength corresponding to a maximum value of the differential values produced during the irradiating of the first light beam;
    irradiating a second light beam onto the substrate, the second light beam having the second wavelength; and
    inspecting defects of the substrate using a third light scattered from the surface of the substrate and a fourth light scattered from the impurities on the substrate.

14. An apparatus for inspecting a substrate for defects, the apparatus comprising:
    a light source for irradiating a plurality of light beams onto the substrate, the plurality of light beams having different wavelengths;
    a detector for detecting light scattered from the substrate;
    an operation unit for comparing first intensities of first lights scattered from a surface of the substrate with second intensities of second lights scattered from impurities on the substrate, for producing differential values of light intensity between the first intensities and the second intensities, respectively, and for selecting a wavelength corresponding to a maximum value of the differential values;
    a controller for controlling the operation of the light source such that the plurality of light beams are sequentially irradiated onto the substrate, and a selected light beam having the selected wavelength is irradiated onto the substrate; and
    an image processing unit for receiving an image representing the substrate using a light scattered from the substrate by irradiation of the selected light beam, and for inspecting defects of the substrate based on the image received.

15. The apparatus of claim 14, wherein the light source includes a tunable optical parametric oscillator laser system.

16. The apparatus of claim 14, wherein the wavelengths of the light beams are in a range of about 250 nm to about 700 nm.

17. The apparatus of claim 14, further comprising a moving stage for supporting the substrate, and moving the substrate so that the light beams scan the substrate.

18. The apparatus of claim 14, further comprising a deflector for deflecting the light beams for scanning the substrate.

19. The apparatus of claim 14, further comprising a beam expander for expanding the light beams, and a focusing lens for focusing the light beams onto the substrate.

20. The apparatus of claim 14, further comprising a display unit for displaying the image.

* * * * *